(12) United States Patent
Shaddox

(10) Patent No.: US 7,280,439 B1
(45) Date of Patent: Oct. 9, 2007

(54) SUNLIGHT SIMULATING MICROPROCESSOR ALARM CLOCK

(76) Inventor: Daniel Edward Shaddox, 10701 SE. Highway 212 # Q7, Clackamas, OR (US) 97015

( * ) Notice: Subject to any disclaimer, the term of this patent is extended or adjusted under 35 U.S.C. 154(b) by 67 days.

(21) Appl. No.: 11/339,265

(22) Filed: Jan. 23, 2006

(51) Int. Cl.
*F21V 23/00* (2006.01)

(52) U.S. Cl. .................. 368/73; 368/256; 362/231; 362/1; 362/2; 362/234

(58) Field of Classification Search .............. 368/12, 368/72–74, 79, 256, 248, 263; 362/231, 362/1, 2, 234
See application file for complete search history.

(56) References Cited

U.S. PATENT DOCUMENTS

| | | | | |
|---|---|---|---|---|
| 4,785,432 A | * | 11/1988 | Havel | 368/82 |
| 5,079,682 A | * | 1/1992 | Roberts | 362/276 |
| 5,309,145 A | * | 5/1994 | Branch et al. | 340/540 |
| 5,327,331 A | * | 7/1994 | Roberts | 362/176 |
| 5,327,403 A | * | 7/1994 | Bond | 368/107 |
| 6,310,833 B1 | * | 10/2001 | Guyett et al. | 368/63 |
| 6,902,296 B2 | * | 6/2005 | Searfoss, III | 362/231 |
| 6,987,710 B2 | * | 1/2006 | Kibiloski et al. | 368/67 |
| 2005/0190654 A1 | * | 9/2005 | Patel | 368/73 |

* cited by examiner

*Primary Examiner*—Gary F. Paumen
(74) *Attorney, Agent, or Firm*—Mark S. Hubert

(57) ABSTRACT

The present invention relates to an improved countermeasure for circadian and sleep disruption as caused by a traditional alarm clock. It incorporates a lighting system at the alarm clock that, prior to the preset waking time, will emit a light that gradually increases in intensity as it changes the ultraviolet spectrum of light it emits, so as to simulate the rising sun. This will ease the waking process for many people, especially those prone to simple disruptions of their circadian regulation. It may also be set to operate in a reverse mode so as to simulate the setting sun thus helping stimulate melatonin production and easing one into sleep.

17 Claims, 3 Drawing Sheets

SUNLIGHT SIMULATING MICROPROCESSOR ALARM CLOCK

FIELD OF THE INVENTION

The present invention relates to an improved alarm clock to aid people who have trouble awakening or sleeping, or for people who's biological circadian rhythm is particularly sensitive. For a predetermined period prior to the alarm setting, it emits an increasing or decreasing intensity light which changes it's wavelength to simulate the colors of the rising or setting sun hereby making it both a safe and practical alternative to sleep disorder medications.

BACKGROUND

Human eyes are sensitive to light in the electromagnetic spectrum labeled "visible light" which corresponds to a wavelength range of 400-700 nanometers (nm) and a color range of violet through red. The visible colors from shortest to longest wavelength are: violet, blue, green, yellow, orange, and red. Sunlight consists of the entire electromagnetic spectrum. Ambient light is the primary stimulus for circadian regulation in humans. Humans have a 24-hour day/night cycle that maintains healthy circadian entrainment. When this cycle is disrupted it results in physiological and behavioral changes that can diminish alertness, cognitive ability and psychomotor performance. This day/night cycle can be disturbed by such things as the seasonal changes in sunrise/sunset, or new waking hours. Studies show that the hormone melatonin, an excess of which deceases the mental acuity and impedes the waking process, may be suppressed by visual stimulation of specific wavelength lighting.

The prior art has focused on maintaining near normal circadian regulation, by utilizing polychromatic fluorescent lighting enriched in the blue monochromatic wavelengths (446-477 nm) for melatonin suppression. These have been found to increase potency for melatonin suppression while keeping the visual experience white. The majority of the studies in this area have been NASA related and aimed at minimizing the detrimental effects of space travel.

Currently there is but a remedial understanding of how photic input regulates the human circadian system, and the effectiveness of this input for different wavelengths and wavelength combinations of light is still a relatively uncharted area. Experimentation with the present sunlight simulating alarm has shown that the introduction of a light into the sleep environment, that changes in it's spectrum and intensity for a predetermined period prior to an audible alarm, results in a much easier experience for arising or inducing sleep. As it now stands, the prior art alarm clocks wake their owner by an audible alarm. The fact that most of these alarms have a snooze feature wherein the alarm repeats itself on timed intervals is proof that this manner of waking is difficult on many people.

Such a device as the present invention, eliminates the pitfalls of the prior art and would be a welcome safe alternative to what the market now offers.

SUMMARY OF THE INVENTION

The general purpose of the present invention, which will be described subsequently in greater detail, is to provide an economical, alarm clock that will ease the difficulty of arising at a preset time.

It has many of the advantages mentioned heretofore and many novel features that result in a new under desk foot warmer which is not anticipated, rendered obvious, suggested, or even implied by any of the prior art, either alone or in any combination thereof.

In accordance with the invention, an object of the present invention is to provide an improved alarm clock designed to condition the human circadian system for an easier waking prior to an audible alarm.

It is another object of this invention to provide an improved alarm clock that utilizes visual stimulation to ease one to sleep.

It is a further object of this invention to provide an inexpensive alarm clock that eases the effort many commonly experience when waking.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements. Other objects, features and aspects of the present invention are discussed in greater detail below.

DETAILED DESCRIPTION

Figure 1:
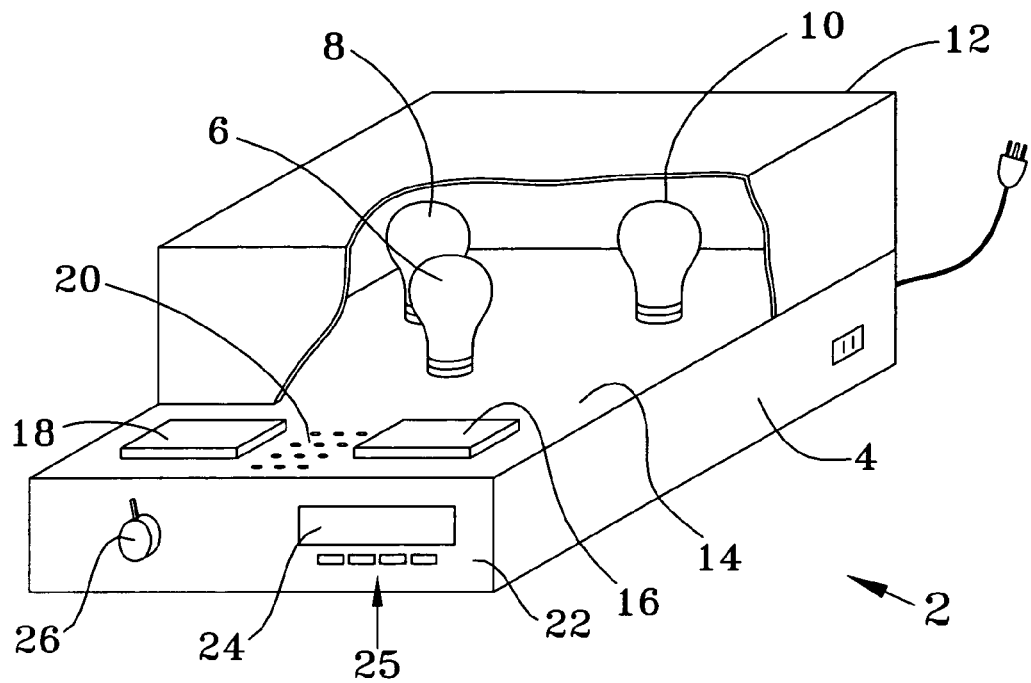
FIG. 1 is a perspective view of the preferred embodiment sunlight simulating microprocessor alarm clock.

The present invention relates to a digital alarm time clock utilizing a light sequencing microprocessor to simulate either the sunrise or sunset as a sleep or waking aid.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings.

The invention is capable of other embodiments and of being practiced and carried out in various ways. Also, it is to be understood that the phraseology and terminology employed herein are for the purpose of descriptions and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The components and operation of a standard digital alarm clock are well known in the industry and the features of time setting, control and display are not novel or unique. It is the microprocessor controlled variable light feature coupled with the digital timepiece that is the subject of this invention.

Figure 2:
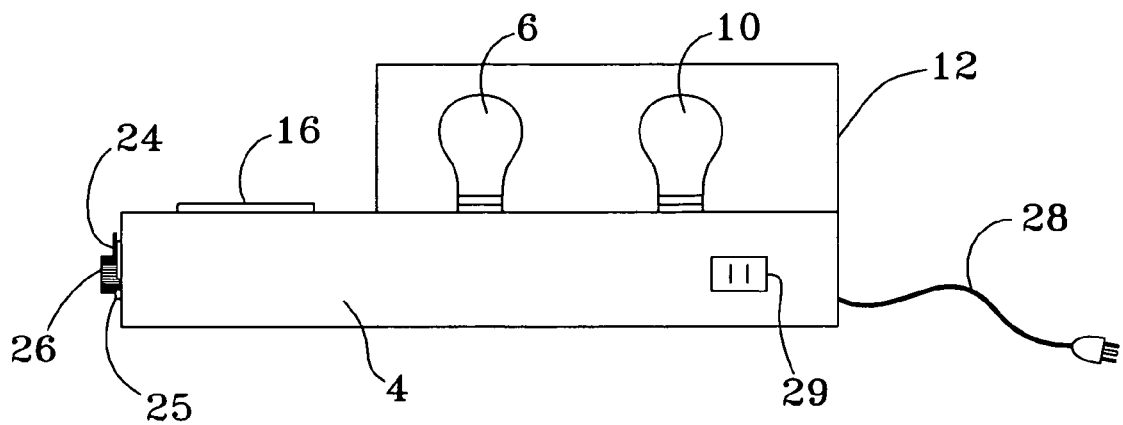
FIG. 2 is a side view of the preferred embodiment sunlight simulating microprocessor alarm clock.

Looking at FIGS. 1 and 2, a perspective and side view of the preferred embodiment sunlight simulating microprocessor alarm clock, it can be seen that the alarm clock 2 has a base 4, which internally houses the electronic components of the digital timepiece, and from which a first light 6, second light 8 and third light 10 are mounted thereon. A cover 12 is mounted onto the top surface 14 of the alarm clock 2 so as to encapsulate the first light 6 second light 8 and third light 10. Cover 12 is translucent but not clear, having a white or "frosted" appearance. In the preferred embodiment, this frosted configuration is primarily for aesthetic purposes and the cover 12 could also be transparent. The snooze button 16, the alarm and light reset button 18 and audible alarm sound holes 20 are also located on the top surface 14. On the face 22 of alarm clock 2, the digital electro optical display 24, time and alarm setting module 25 and mode selection switch 26 are located. A means for connection to an electrical power supply 28 extends from the alarm clock. An auxiliary electrical outlet 29 is located on the base 4 of the alarm clock 2. Inside the base 4 are the timepiece electronics, a piezoelectric buzzer and the light sequencing microprocessor mounted on a circuit board whereon the majority of physical electrical connections are made. The operation, design, construction, programming and connection of the individual electrical components are well known in the industry.

The three lights are of varying colors and intensities. First light 6 is the lowest lumen incandescent light bulb. It is blue in color and has a wattage in the 5-40 watt range. Second light 8, is the medium lumen incandescent light bulb, is red in color and has a wattage in the 20-75 watt range. Third light 10 is the highest lumen incandescent light bulb that is red in color and has a wattage in the 60-150 watt range. Experimentation has shown that 20, 40 and 60 watt bulbs work satisfactorily when the alarm clock 2 is placed on a night stand adjacent the user's bed. However, these values are nominal and the actual wattage of the bulbs used will vary with the size of the room and the distance from the user.

In operation, the snooze button 16 temporarily switches off the audible alarm for a preset time, the light reset button 18 switches off the lights and audible alarm, and the mode selection switch 26 toggles between the sleep mode, the wake mode, the sleep/wake mode and off. The time and alarm setting module 25 has buttons that are of conventional design and may incorporate a time set selection button 30, an alarm set selection button 32, an up button 34 and a down button 36. The electro optical display 24 and time and alarm setting module 25 function as do those of a conventional digital alarm clock but allow for the setting of both a sleep time and a wake time.

There are four modes for the operation of alarm clock 2. They are wake mode, sleep mode, wake and sleep mode and off. The selection of these modes is accomplished through the rotation of mode selection switch 26 about its four contact positions.

When a wake time has been set and the wake mode selected, at a discrete timed interval prior to the wake time, blue light 6 turns on. After a timed interval, red light 8 turns on and blue light 6 turns off, and after a second timed interval white light 10 turns on and red light 8 turns off. After a third timed interval, the audible alarm sounds. The operation of the alarm button 16 is to reset the audible alarm for a repeat function after a brief period, generally in the 5 to 15 minute range. The light reset button 18 switches off the lights and the audible alarm until the next cycle of operation commences. The first (blue) light 6 comes on 45-60 minutes before the audible alarm. The second (red) light 8 comes on 15-20 minutes later and the third (white) light 10 comes on 15-20 minutes before the audible alarm sounds.

In the preferred embodiment 2, the blue, red and white light bulb wattages are respectively 20, 40 and 60 watts, and the timed intervals between the sequencing of the lights are 15 minutes each. The color sequencing simulates, to an extent, the changing colors and intensity of the rising sun.

When a sleep time has been set and the sleep mode selected, at a discrete timed interval prior to the wake time, white light 10 turns on. After a timed interval, red light 8 turns on and white light 10 turns off, and after a second timed interval blue light 6 turns on and red light 8 turns off. After a third timed interval, blue light 6 turns off. The operation of the sleep mode follows the reverse sequencing of the wake mode. It is used to lull children to sleep at night. The color sequencing simulates to an extent the changing colors of the setting sun. The timing intervals are the same as used in the wake mode.

In the wake and sleep mode, the alarm clock 2 functions twice a day, as detailed above. In the off mode the light feature is disabled.

The preferred embodiment may also be used with three varying wattage blue lightbulbs. This is an option for people with severe sleeping disorders. Studies have shown that the blue monochromatic wavelengths (446-477 nm) are the most potent for melatonin suppression.

Figure 3:
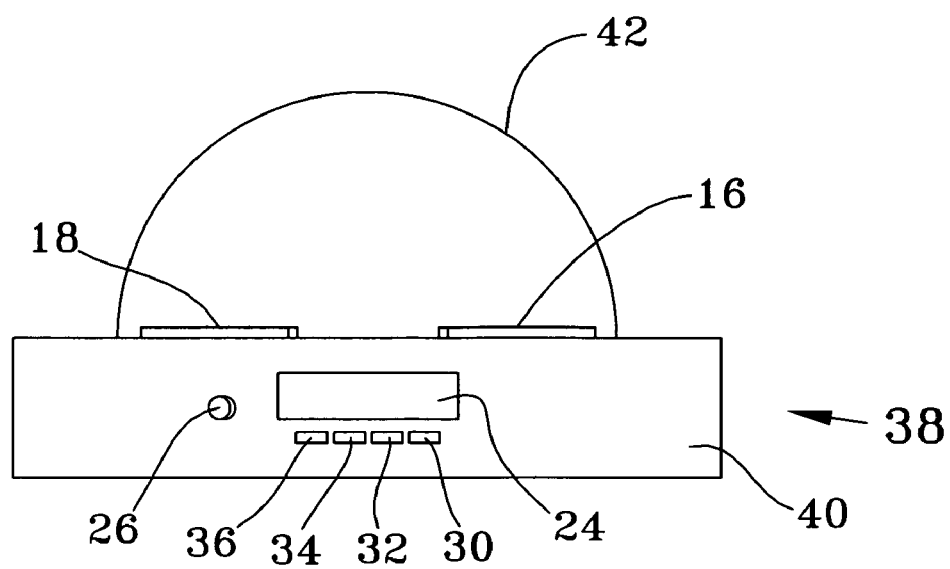
FIG. 3 is a perspective view of the first or second alternate embodiment sunlight simulating microprocessor alarm clock.
Figure 4:
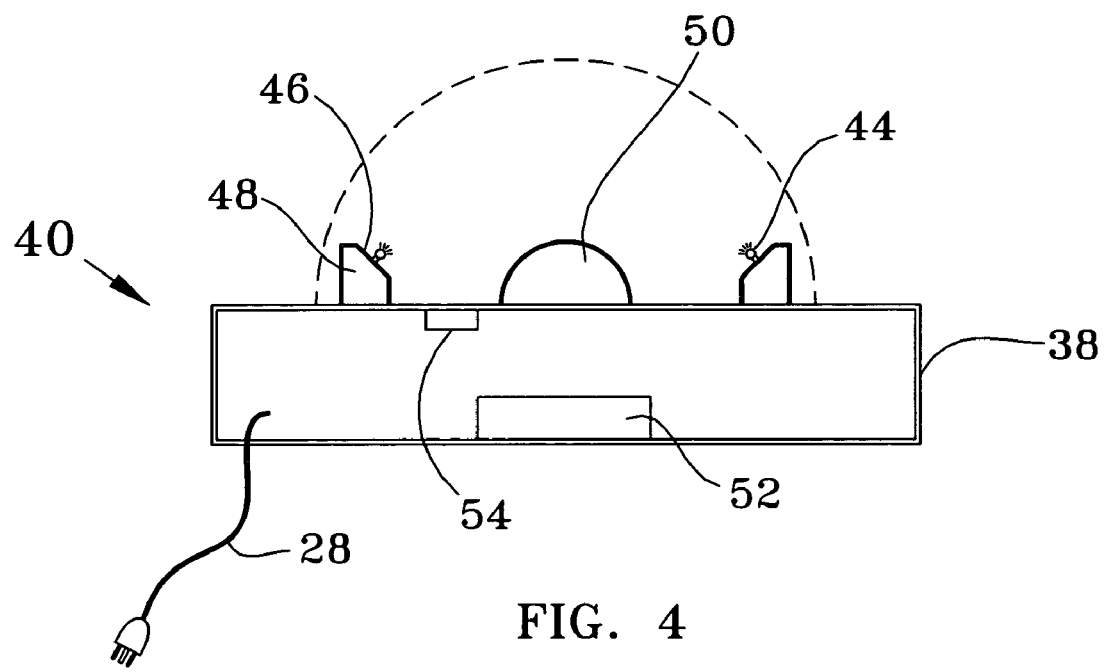
FIG. 4 is a cross sectional view of the first alternate embodiment sunlight simulating microprocessor alarm clock.

Looking now at FIGS. 3 and 4, the first alternate embodiment alarm clock 38 it can be seen that alternate base 40 houses substantially similar components as the preferred embodiment alarm clock 2. Looking at FIG. 5 it can be seen that the physical configuration of alternate base 40 is circular rather than square as base 4. Alternate cover 42 is a hemispherical dome that is translucent and preferably frosted white. The first alternate embodiment alarm clock 40 uses light emitting diodes (LEDS) 44 for a light source. The LEDS 44 are mounted on the beveled inner face 46 of ring 48. Ring 48 is equidistant from a centrally located diffusing reflector 50. Reflector 50 is of a hemispherical geometry and has an outer reflective surface. The cross sectional view of FIG. 4 shows the microprocessor 52 and piezoelectric buzzer 54 housed inside alternate base 40.

Figure 5:
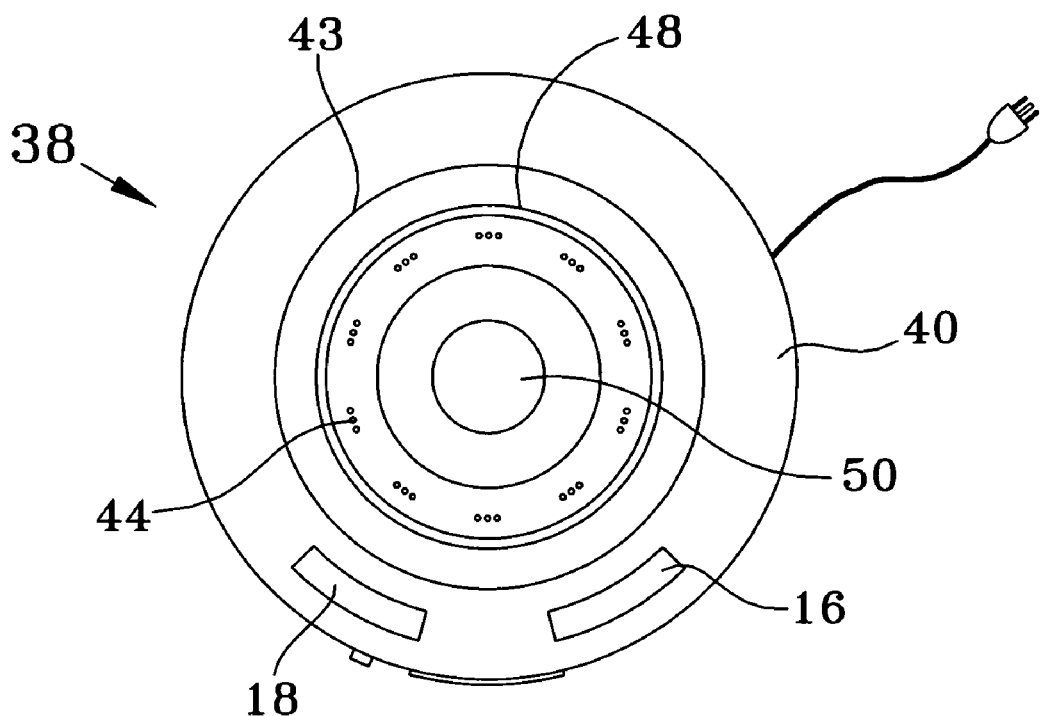
FIG. 5 is a top view of the first alternate embodiment sunlight simulating microprocessor alarm clock with it's cover removed.

FIG. 5 shows a top view of the first alternate embodiment alarm clock 38 with it's cover removed. There is a recess 43 that the edge of cover 42 sits in when the cover 42 is in place. It can be seen that LEDS 44 are arranged in groupings of 3. In each group there is a red, green and blue LED.

Figure 6:
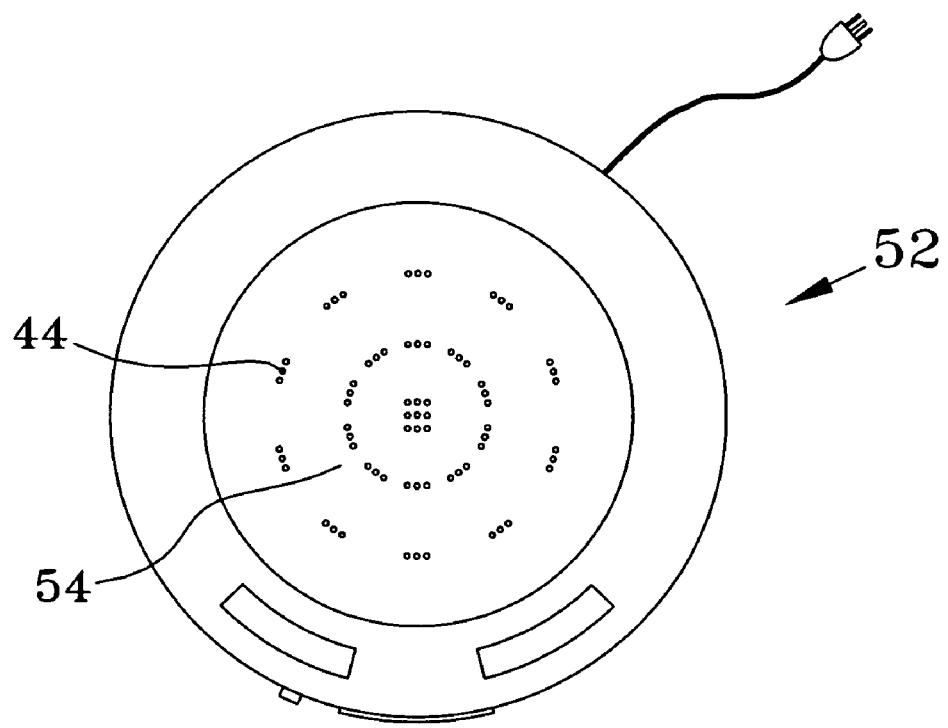
FIG. 6 is a top view of the second alternate embodiment sunlight simulating microprocessor alarm clock with it's cover removed.

FIG. 6 shows the second alternate embodiment alarm clock 52. It can be seen that it differs from first alternate embodiment alarm clock since it has no ring or reflector and it contains many more LEDS 44. Note the LEDS 44 are directly mounted to the base top surface 54.

In operation, the clock (timepiece) features of first and second alternate embodiment alarm clocks do not differ from that of the preferred embodiment. The difference lies in the emission of the light. The alternate embodiments radiate light that gradually changes in wavelength and intensity so as to approximate the rising or setting sun. The light emitted gradually changes from a wavelength of 400 to 700 nanometers (nm) or from 700 to 400 nm depending on whether it is in the wake or sleep mode. The microprocessor 52 is configured to algorithmically power the various LEDS in combination so as to alter which LEDS or combination of LEDS are being illuminated as well the intensity of the illuminations of the various LEDS. Such algorithms are well known in the art. The required electrical components such as timer chips, current-limiting resistors and current-amplifying transistors necessary to allow this type of illumination from LEDS or superbright LEDS are well known in the art and not discussed herein.

In elementary color theory we see color as a combination of three colors, red, green, and blue. Thus by varying the combination and intensity of these three colors we can achieve the entire spectrum of colors. The mechanics of this, simplified, are accomplished by utilizing a microchip that provides the algorithm to drive a timer chip that pulses the three different color LEDS fast enough to make the three different colors visually stable (this may or may not utilize a trio of shift registers). The number of pulses sent to each light determine the brightness of that LED. The combination of the various intensities of red green and blue colors emitted, give the visually perceived light. The algorithm adjusts these parameters so that the perceived color simulates either the rising or setting sun.

The covers 12 and 42 are translucent rather than clear. In the alternate embodiment this serves to further blend or mix the perceived light. In the preferred embodiment, the cover 12 serves an aesthetic purpose to hide the lightbulbs. However in the alternate embodiments, this blending feature is critical and is also accomplished in part by the reflector 50. Without the reflector 50 and or the alternate cover 42, zones of the red, green and blue colors may be perceived.

In the first alternate embodiment alarm clock 38 the LEDS 44 are mounted on the beveled inner face 46 of ring 48 so as to project their light toward a centralized location in the vicinity of the reflector 50. The reflector 50 has a reflective surface 26. It may by highly polished and smooth, or mirrorlike in finish. Ring 46 is equidistant from a centrally located diffusing reflector 50. This geometrical configuration is used to ensure the maximum amount of light mixing by direct interference with the light from opposing LEDS on the ring 48 and from reflective mixing of the light bounced off of the reflector 50. The resultant mixed light in combination with the cover 42 acts to defeat localized color zones and to more effectively combine the three colors when forming white light.

The second embodiment alarm clock 52 utilizes more LEDS 44 and the LEDS are of a lower power than the LEDS 44 used in the first alternate embodiment. The LEDS 44 are directly mounted to the to the base top surface 54. With the lower power LEDS (reduced light intensity) and the increased number of LEDS, mixing of the light is not a problem, however power consumption rises.

Although not shown, a high illumination version of this second alternate embodiment is possible by increasing the number of LEDS 44 mounted on the base top surface 54 and or by utilizing superbright LEDS.

With the use of this invention as shown and described above, it may be possible to optimize the light spectrum as a melatonin suppression or production countermeasure for sleep and circadian disturbances at the waking or sleeping periods.

The above description will enable any person skilled in the art to make and use this invention. It also sets forth the best modes for carrying out this invention. There are numerous variations and modifications thereof that will also remain readily apparent to others skilled in the art, now that the general principles of the present invention have been disclosed.

Having thus described the invention, what is claimed as new and desired to be secured by Letters Patent is as follows:

1. An improved alarm clock that emits light of various wavelengths and intensities for a predetermined period of time prior to the reaching of at least one time dependent alarm setpoint comprising:
   a base adapted for housing all components of said alarm clock;
   an electro-optical display adapted to display the time set on said alarm clock and said alarm setpoints;
   a time and alarm setting module adapted to set the time and said alarm setpoints;
   an electro-audible alarm;
   at least one light emitting element;
   a microprocessor means adapted to sequence the color and intensity of said emitted light in conformance with at least one programed algorithmic cycle responding to said alarm setpoints;
   a first contact means for silencing said electro-audible alarm for a predetermined time period,
   a second contact means for switching off said light emitting element, silencing said electro-audible alarm and resetting said microprocessor cycle; and
   a means for connecting said alarm clock to a power supply.

2. The improved alarm clock of claim 1 wherein the number of said light emitting elements is at least three.

3. The improved alarm clock of claim 2 wherein said microprocessor means has a first algorithmic cycle that adjusts the various wavelengths and intensities of said light emitting elements to simulate the changing visual colors or the rising sun; and a second algorithmic cycle that adjusts the various wavelengths and intensities of said light emitting elements to simulate the changing visual colors or the setting sun.

4. The improved alarm clock of claim 3 further comprising a mode selection switch adapted to allow operation of said microprocessor means' first algorithmic cycle, second algorithmic cycle, both first and second algorithmic cycles or none of said cycles.

5. The improved alarm clock of claim 4 wherein said light emitting elements are a blue light emitting incandescent lightbulb, a red light emitting incandescent lightbulb and a white light emitting incandescent lightbulb.

6. The improved alarm clock of claim 5 wherein said blue light emitting incandescent lightbulb has a 5 to 40 watt rating, said red light emitting incandescent lightbulb has a 20 to 75 watt rating and said white light emitting incandescent lightbulb has a 60 to 150 watt rating.

7. The improved alarm clock of claim 6 wherein said blue light emitting incandescent lightbulb has a 20 watt rating, said red light emitting incandescent lightbulb has a 40 watt rating and said white light emitting incandescent lightbulb has a 60 watt rating.

8. The improved alarm clock of claim 7 wherein there is a waking time setpoint and a sleeping time setpoint.

9. The improved alarm clock of claim 8 wherein said microprocessor means turns on said blue light emitting incandescent lightbulb for the period of time 45 to 30 minutes before said waking time setpoint, turns on said red light emitting incandescent lightbulb for the period of time 30 to 15 minutes before said waking time setpoint, and turns on said white light emitting incandescent lightbulb 15 minutes before said waking time setpoint.

10. The improved alarm clock of claim 9 wherein said microprocessor means turns on said white light emitting incandescent lightbulb for the period of time 45 to 30 minutes before said sleeping time setpoint, turns on said red light emitting incandescent lightbulb for the period of time 30 to 15 minutes before said sleeping time setpoint, and turns on said blue light emitting incandescent lightbulb 15 minutes before said sleeping time setpoint until said sleeping time setpoint is reached.

11. The improved alarm clock of claim 10 further comprising a translucent cover adapted to reside on said base and cover said light emitting elements.

12. The improved alarm clock of claim 4 wherein said light emitting elements are groupings of a blue light emitting diode, a red light emitting diode and a green light emitting diode which are illuminated by said microprocessor means so as to gradually increase the wavelength of visible light and the illumination level during the 45 minute period of time preceding the waking time setpoint.

13. The improved alarm clock of claim 12 wherein said light emitting diodes are illuminated by said microprocessor means so as to gradually decrease the wavelength of visible light and the illumination level during the 45 minute period of time preceding the sleeping time setpoint.

14. The improved alarm clock of claim 13 further comprising a translucent cover adapted to reside on said base and cover said light emitting elements.

15. The improved alarm clock of claim 14 further comprising an LED mounting ring affixed to a top of said base, and said ring having an inwardly angled face wherein said LEDS are mounted.

16. The improved alarm clock of claim 15 further comprising a light reflector centrally located on said top of said base and residing at the midpoint of said ring wherein said reflector has a polished, light reflective outer surface.

17. The improved alarm clock of claim 16 wherein said an electro-audible alarm emits an audible alarm when said waking time setpoint has been reached.

\* \* \* \* \*